(12) United States Patent
Patel et al.

(10) Patent No.: US 12,156,739 B2
(45) Date of Patent: Dec. 3, 2024

(54) METHODS AND SYSTEMS FOR SELECTING AN INJECTION SITE

(71) Applicant: Eli Lilly and Company, Indianapolis, IN (US)

(72) Inventors: Hemant Thakorbhai Patel, Indianapolis, IN (US); Louis Stevens Somlai, Zionsville, IN (US); Adam Nathaniel Wiesler, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/006,185

(22) PCT Filed: Jul. 14, 2022

(86) PCT No.: PCT/US2022/037041
§ 371 (c)(1),
(2) Date: Jan. 20, 2023

(87) PCT Pub. No.: WO2023/287934
PCT Pub. Date: Jan. 19, 2023

(65) Prior Publication Data
US 2023/0293101 A1 Sep. 21, 2023

Related U.S. Application Data

(60) Provisional application No. 63/222,456, filed on Jul. 16, 2021.

(51) Int. Cl.
*A61B 5/00* (2006.01)
(52) U.S. Cl.
CPC .......... *A61B 5/4824* (2013.01); *A61B 5/7405* (2013.01); *A61B 5/742* (2013.01); *A61B 5/7455* (2013.01)

(58) Field of Classification Search
CPC ..... A61B 5/4824; A61B 5/7405; A61B 5/742; A61B 5/7455
See application file for complete search history.

(56) References Cited

U.S. PATENT DOCUMENTS

| 7,740,612 B2 | 6/2010 | Hochman |
| 8,734,394 B2 | 5/2014 | Adams et al. |

(Continued)

FOREIGN PATENT DOCUMENTS

| CH | 715791 A2 | 7/2020 |
| CN | 105979992 A | 9/2016 |

(Continued)

OTHER PUBLICATIONS

Patent Cooperation Treaty, International Search Report of the International Searching Authority pertaining to International Application No. PCT/US2022/037041; International Filing Date: Jul. 14, 2022; Date of Mailing: Oct. 26, 2022.

(Continued)

*Primary Examiner* — Andrey Shostak
(74) *Attorney, Agent, or Firm* — Arthur Shum

(57) ABSTRACT

Methods and systems are provided for evaluating injection sites on a body of a patient. The methods/systems may instruct a patient to place one or more capacitance sensors in contact with a potential injection site on the body of the patient. The methods/systems may also comprise using a processing circuit to receive data indicative of a capacitance of body tissue at the potential injection site, as measured by the one or more capacitance sensors. The methods/systems may also comprise generating, using the processing circuit, an indication of a level of pain that would be expected to be experienced by the patient from a potential injection at the potential injection site based on the received capacitance.

9 Claims, 12 Drawing Sheets

(56) References Cited

U.S. PATENT DOCUMENTS

| | | | |
|---|---|---|---|
| 10,561,800 B2 | 2/2020 | Marlin et al. | |
| 10,603,429 B2 | 3/2020 | Dantsker | |
| 10,716,503 B2 | 7/2020 | Addison et al. | |
| 11,123,488 B2 | 9/2021 | Adams et al. | |
| 2005/0177061 A1* | 8/2005 | Alanen | A61B 5/4878 |
| | | | 600/547 |
| 2006/0015058 A1 | 1/2006 | Kellogg | |
| 2009/0275823 A1* | 11/2009 | Ayati | A61B 5/150389 |
| | | | 600/424 |
| 2015/0045729 A1* | 2/2015 | Denzer | A61M 5/50 |
| | | | 604/110 |
| 2015/0265208 A1 | 9/2015 | Addison | |
| 2015/0273151 A1* | 10/2015 | McLoughlin | A61M 5/002 |
| | | | 604/66 |
| 2017/0007763 A1* | 1/2017 | McLoughlin | A61M 5/20 |
| 2018/0368761 A1* | 12/2018 | Addison | A61B 5/4821 |
| 2019/0076604 A1 | 3/2019 | Fiedler et al. | |
| 2019/0321565 A1* | 10/2019 | Chanie | A61M 5/42 |
| 2019/0365998 A1 | 12/2019 | Henderson et al. | |
| 2020/0197626 A1 | 6/2020 | Denzer et al. | |
| 2020/0384188 A1 | 12/2020 | Becker et al. | |
| 2021/0077723 A1* | 3/2021 | Marcoz | A61M 5/31575 |
| 2022/0016347 A1* | 1/2022 | Le Masne | A61M 5/2033 |
| 2022/0347398 A1* | 11/2022 | Paramanandam | A61M 5/5086 |

FOREIGN PATENT DOCUMENTS

| | | |
|---|---|---|
| EP | 3381493 A1 | 10/2018 |
| WO | 9410987 | 5/1994 |
| WO | 2015071390 | 5/2015 |
| WO | 2020142544 | 7/2020 |

OTHER PUBLICATIONS

Patent Cooperation Treaty, Written Opinion of the International Searching Authority pertaining to International Application No. PCT/US2022/037041; International Filing Date: Jul. 14, 2022; Date of Mailing: Oct. 26, 2022.

O'goshi, K., et al., "Inter-Instrumental Variation of Skin Capacitance Measured With the Corneometer®," Skin Research and Technology 2005; vol. 11, pp. 107-109.

* cited by examiner

METHODS AND SYSTEMS FOR SELECTING AN INJECTION SITE

BACKGROUND OF THE DISCLOSURE

Injection devices in the form of a syringe or which include a syringe are widely employed by medical professionals and patients who self-medicate. Patients suffering from a number of different diseases may frequently inject themselves with medication, and a variety of devices have been developed to facilitate such self-medication. In one example, the use of an automatic injection device which includes mechanisms to perform some of the steps of the injection process renders it more convenient for a patient to self-medicate particularly by patients with limited manual dexterity. Automatic injection devices may be single use devices that are disposed after use.

SUMMARY

The inventors have appreciated that using injection devices to perform injections may cause pain for the patient at the injection site, potentially at the time of injection, and/or within a number of hours (e.g., 1-3 hours) after the injection. The inventors have also appreciated that injecting at some injection sites may lead to less injection site pain than other injection sites. Which injection sites lead to less pain may differ from patient to patient based on the physiology of the patients' bodies. It would therefore be desirable to provide personalized guidance to the user and/or patient regarding which injection sites may lead to less pain.

According to an exemplary embodiment of the present disclosure, a method for evaluating injection sites on a body of a patient is provided, the method comprising: receiving, at a processing circuit in communication with one or more capacitance sensors positioned at a potential injection site on the body of the patient, a signal indicative of a capacitance of body tissue at the potential injection site measured by the one or more capacitance sensors; and determining, by the processing circuit based on the received signal, a level of expected pain that would be experienced by the patient from a prospective injection at the potential injection site.

According to another embodiment of the present disclosure, a processing device for evaluating injection sites on a body of a patient is provided, the device comprising: a memory storing instructions; a communication interface configured to receive data from one or more capacitance sensors; a processing circuit configured to execute the instructions to: receive, from the one or more capacitance sensors via the communication interface, data indicative of a capacitance of body tissue at a potential injection site on the body of the patient measured by the one or more capacitance sensors, store the received data indicative of the capacitance in the memory, and determine, based on the received data indicative of the capacitance, a level of expected pain that would be experienced by the patient from a prospective injection at the potential injection site.

According to yet another embodiment of the present disclosure, a system for evaluating injection sites on a body of a patient is provided, the system comprising: an injection device comprising: a needle for delivering a medication to the patient via an injection, one or more capacitance sensors, and a wireless transmitter; and an external device comprising: a memory storing instructions; a communication interface configured to receive data from the wireless transmitter of the injection device; and a processing circuit configured to execute the instructions to: receive, via the communication interface, data from the injection device indicative of a capacitance of body tissue at a potential injection site on the body of the patient measured by the one or more capacitance sensors, store the received data indicative of the capacitance in memory, and determine, based on the received data indicative of the capacitance, a level of expected pain that would be experienced by the patient from a prospective injection by the injection device at the potential injection site.

In some embodiments, an exemplary advantage of the disclosed methods and systems is that they provide personalized guidance to patients regarding which injection sites on his/her body are likely to lead to less injection site pain. Other advantages will be recognized by those of ordinary skill in the art.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
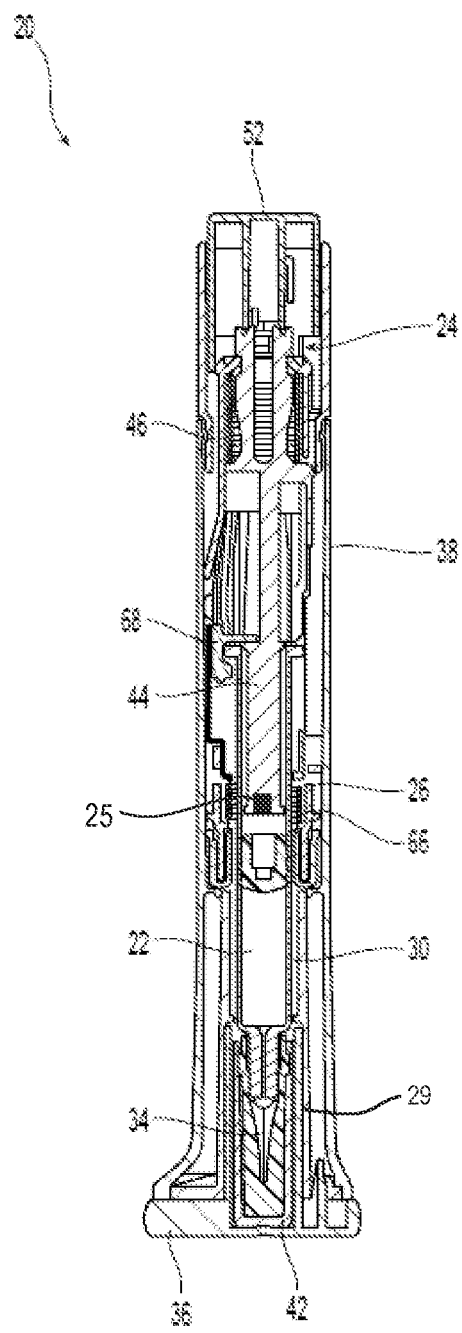
FIG. 1 is a cross sectional view of an injection device prior to use according to an exemplary embodiment.
Figure 2:
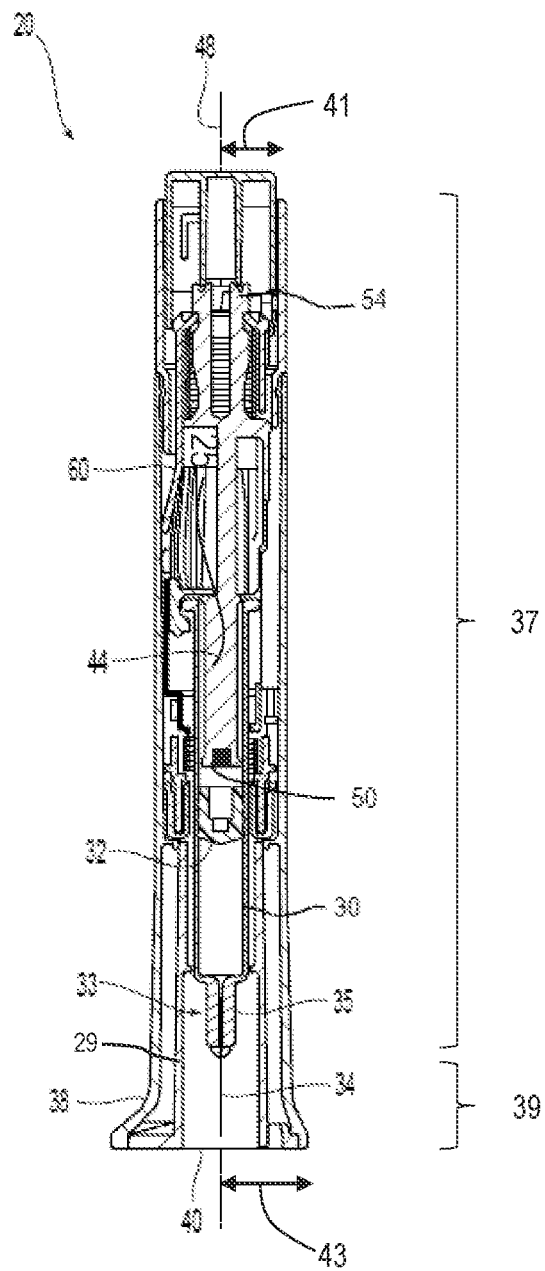
FIG. 2 is a cross sectional view of the injection device of FIG. 1 with the syringe assembly in a storage position and ready for an injection event.
Figure 3:
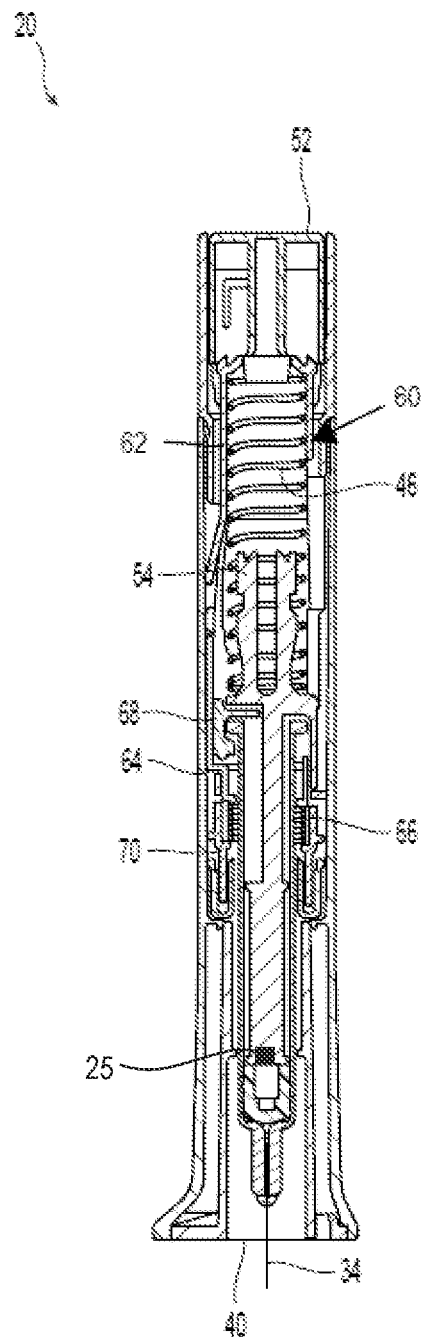
FIG. 3 is a cross sectional view of the injection device of FIG. 1 with the syringe assembly in an injection position.

In FIGS. 1-3, a medication injection device 20 is depicted in various operational states. One example of such a device and its operation is described in U.S. Pat. No. 8,734,394 B2 issued May 27, 2014 to Adams et al. and in U.S. Patent App. Pub. No. 2021/0093784 A1 published Apr. 1, 2021 to Adams et al., the entire disclosure of each of which is hereby incorporated herein by reference. Device 20 includes a syringe assembly 22, a drive mechanism 24, and a retraction mechanism 26, and may include one or more main printed circuit boards (PCBs) 500 shown later, for example, in FIGS. 5, 6A, and 6B. Syringe assembly 22 includes a barrel 30 forming a container body for holding a medication, and a piston 32 disposed within the barrel 30 for driving the medication outside the barrel. Syringe assembly 22 also includes a needle assembly 33 having a hollow injection needle 34 and a needle hub 35 which mounts needle 34 to syringe barrel 30. A lower body support member 29 (depicted in FIG. 5) coupled to device housing 38 surrounds needle 34. Advancing piston 32 within barrel 30 toward needle 34 dispenses medication through needle 34.

Devices described herein, such as device 20, may further comprise a medication, such as for example, within the syringe barrel 30. In another embodiment, a system may comprise one or more devices including device 20 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, combined GIP/GLP-1 agonists such as tirzepatide, oxyntomodulin analogs, oxyntomodulin derivatives, therapeutic antibodies including but not limited to IL-23 antibody analogs or derivatives, such as mirikizumab, IL-17 antibody analogs or derivatives, such as ixekizumab, therapeutic agents for pain-related treatments, such as galcanzeumab or lasmiditan, and any therapeutic agent that is capable of delivery by the devices described herein. The medication as used in the device may be formulated with one or more excipients. The device is operated in a manner generally as described above by a user, caregiver or healthcare professional to deliver medication to a patient. As used herein, the term "user" may refer to an operator of the devices described herein, and the term "patient" may refer to a person receiving the medication. In some cases, the user and the patient may be the same person (e.g., the patient is operating the devices described herein to give him/herself an injection). In other cases, the user and the patient may be different persons (e.g., the user may be a person providing care to the patient).

FIG. 1 illustrates device 20 in its initial, pre-use configuration. Here, an end cap 36 is secured to lower body support member 29 (which is in turn coupled to device housing 38). End cap 36 covers a proximal end opening 40 in housing 38. As used herein, distal and proximal refer to axial locations relative to an injection site when the apparatus is oriented for use at such site, whereby, for example, proximal end of the housing refers to the housing end that is closest to such injection site, and distal end of the housing refers to the housing end that is farthest from such injection site. Also as used herein, an "injection site" may refer to the exact spot on a patient's body that is injected by a needle, as well as body tissue surrounding the spot where the needle injects (e.g., within 1-5 cm or 1-10 cm of the spot where the needle punctures the patient's skin). Housing 38 may be formed from a plastic material and is shown extending generally longitudinally between a distal end in close proximity to an actuating button 52 and a proximal end in close proximity to the proximal end opening 40 along a longitudinal axis 48. As shown in FIG. 2, housing 38 may comprise a user-graspable portion 37 configured to be grasped by a hand of a user, the user-graspable portion 37 extending a radial distance 41 outward from longitudinal axis 48. In some embodiments, the radial distance 41 may be between 5-10 mm in length (e.g., in some embodiments, 5-8 mm may be a suitable length). Also as shown in FIG. 2, housing 38 may also comprise an outwardly-flared end portion 39 at a proximal end of the housing adjacent the proximal opening 40. The end portion extends a radial distance 43 outward from longitudinal axis 48 that is greater than the radial distance 41. In some embodiments, the radial distance 43 may be greater than 10 mm in length. For example, in some embodiments, the radial distance 43 may be between 10-20 mm in length (e.g., in some embodiments, 15-20 mm may be a suitable length). End portion 39 may slope smoothly radially outward from the user-graspable portion 37, as shown in FIGS. 1-3. In other embodiments, end portion 39 may take the form of other shapes. End portion 39 may take on any shape that extends a radial distance 43 away from longitudinal axis 48 that is greater than the radial distance 41 of the user-graspable portion.

A needle guard 42 is mounted on syringe assembly 22 and covers and surrounds needle 34. End cap 36 and needle guard 42 protect the user from accidental needle pricks and also protect needle 34 from damage. When using device 20 to dispense medication, for example, injecting the medication into a patient, end cap 36 and needle guard 42 are first removed. FIG. 2 illustrates device 20 after removal of end cap 36 and needle guard 42 from syringe assembly 22, wherein the syringe assembly is in a storage position and device 20 is ready for a dispensing event.

Syringe assembly 22 is moveable relative to the injection device 20 between a storage position and an injection position. FIG. 3 illustrates device 20 after the syringe assembly 22 has been moved relative to device 20 to an injection position from its storage position that is shown in FIG. 2. In the storage position (FIGS. 1 and 2), needle 34 is retracted to a position such that needle 34 is disposed within housing 38 of device 20. In the injection position (FIG. 3), needle 34 projects outwardly from housing 38 beyond proximal opening 40 in the proximal direction parallel to longitudinal axis 48 whereby needle 34 may be inserted into a patient.

Drive mechanism 24 includes a plunger 44 which engages piston 32. Drive mechanism 24 includes a spring 46 that drives plunger 44 in a translational movement. In the illustrated embodiment, spring 46 advances plunger 44 along a linear path defined by the longitudinal axis 48 of device 20. As plunger 44 is advanced, foot 50 of plunger 44 contacts piston 32. As the plunger 44 is further advanced, syringe assembly 22 is advanced along axis 48 from its storage position to its injection position. After advancement of syringe assembly 22 to its injection position, the continued proximal advancement of plunger 44 advances piston 32 proximally within barrel 30 from its initial piston position (shown in FIGS. 1 and 2) to its final piston position (shown FIG. 3) to cause medication to be dispensed from needle 34 in a dispensing event. Prior to any dispensing of medication and when syringe barrel 30 holds the full original volume of medication, piston 32 will be in its initial piston position. After advancing piston 32 the full extent of its travel length toward needle assembly 33, piston 32 will be in its final piston position proximate needle assembly 33 and the medication from within barrel 30 will have been discharged. In a single use, syringe assembly 22 will hold a single dose of medication which will be delivered in a single injection event and piston 32 will be advanced from its initial piston position to its final piston position in that single injection event to thereby deliver the entire single dose contents of syringe assembly 22. While the device is shown as a single use device, device 20 may also be configured as a multiple-use device with appropriate modifications.

The advancement of plunger 44 will generally not result in the dispensing of medication from syringe assembly 22 until after syringe assembly 22 has been advanced to the injection position. There are factors that may inhibit the medication from being dispensed before the syringe is advanced to the injection position. A factor may be the friction between piston 32 and barrel 30. Typically, piston 32 will be formed out of a rubber material and barrel 30 will be glass. The frictional resistance between these two components may be sufficient to prevent the advancement of piston 32 within barrel 30 until syringe assembly 22 is advanced to its injection position and engagement with a suitable stop member prevents the further advancement of syringe assembly 22. Additionally, the medication within the syringe may be somewhat viscous and thereby somewhat resistant to flowing out of needle 34. If necessary, modification of piston 32 and syringe barrel 30 to alter the frictional resistance of dispensing motion of the engagement member 32 relative to syringe barrel 30 may limit or prevent the premature dispensing of medication before container 22 reaches its injection position.

To activate drive mechanism 24, a person depresses actuating button 52 at the distal end of device 20. Depressing button 52 disengages one or two elongate prongs 54 on plunger 44 from a shuttle assembly 60 thereby allowing spring 46 to axially advance plunger 44. Spring 46 has a helical shape and surrounds prongs 54. The proximal end of spring 46 biasingly engages a flange on plunger 44.

Shuttle assembly 60 may include an upper shuttle member 62 and a lower shuttle member 64. Shuttle members 62, 64 are fixed together in the final assembly. In the final assembly, upper shuttle member 62 captures button 52 and spring 46 limiting the axial movement of these parts in the distal direction. Prongs 54 engage surfaces on upper shuttle 62 when the device is in the condition shown in FIGS. 1 and 2. Depressing button 52 causes tabs on button 52 to engage ramps (not shown) on prongs 54 to bias prongs 54 inwardly to disengage prongs 54 from upper shuttle member 62. After prongs 54 have been disengaged, spring 46 exerts a biasing force on flange 56 to advance plunger 44 from the position shown in FIG. 2 to the position shown in FIG. 3. As plunger 44 is advanced, it moves syringe assembly 22 to the injection position and then advances piston 32 to dispense medication as discussed above.

After the dispensing event is complete, retraction mechanism 26 optionally moves syringe assembly 22 from the injection position shown in FIG. 3 back to a retracted position. More specifically, the retraction mechanism is adapted to move the medication container from the injection position to the retracted position in a retraction movement. The retracted position may be similar to the storage position in that the syringe assembly is drawn back into the housing 38 such that needle 34 no longer projects proximally from proximal opening 40 and is disposed entirely within housing 38. In some embodiments, the retracted position may be the same as the storage position. In other embodiments, however, a syringe assembly 22 in the retracted position may be located slightly proximal or distal to a syringe assembly in the storage position. In the illustrated embodiment, the retraction mechanism includes a spring 66, a syringe carrier and a rotary member 70 that acts as a follower. In yet other embodiments, the device 20 may include no retraction mechanism 26 such that the syringe assembly remains in its injection position indefinitely after the medication has been dispensed, until the syringe assembly is manually removed or repositioned by a user.

Plunger 44 may include an outrigger (not shown) which unlocks rotary member 70 as plunger 44 nears the end of its travel in the proximal direction. Rotary member 70 is rotationally secured to lower shuttle member 64 by engagement between a latch and a latching recess in lower shuttle member 64. The outrigger unlocks member 70 by depressing the latch. Spring 66 is torsionally preloaded and has one end engaged with member 70 and an opposite end engaged with shuttle assembly 60. Upon depression of the latch, spring 66 causes member 70 to rotate.

Member 70 is rotatable within housing 38 but is not axially moveable relative to housing 38. Other embodiments may include a member 70 that is also axially movable. The rotation of member 70 serves as a delay mechanism to prevent retraction mechanism 26 from retracting syringe assembly 22 until after the syringe assembly has finished delivering its dose of medication. The speed of rotation of member 70 may be adjusted by adjusting a viscosity of grease disposed on or around surfaces of member 70 that are in contact with housing 38—a more viscous grease results in slower rotation, while a less viscous grease results in faster rotation. A radial flange on rotary member 70 may engage a ledge within housing member 38 to limit the proximal movement of member 70. Spring 66 may exert an axial force, torsional force, or both forces on member 70 to bias member 70 proximally to thereby maintain member 70 in an axial position where the radial flange of member 70 engages the interior ledge of housing member 38.

Shuttle assembly 60 may include axially extending channels or ribs that engage corresponding features on housing member 38 that allow shuttle assembly 60 to move axially within housing 38 but which prevent the relative rotation of shuttle assembly 60 relative to housing member 38. Shuttle assembly 60 is biased in the distal direction by spring 66 but is prevented from moving distally by engagement of a latch (not shown) before activation of drive mechanism 24. When rotary member 70 completes its rotation, it disengages the aforementioned latch, thus allowing shuttle assembly 60 to move distally under the biasing force of spring 66.

As shuttle assembly 60 moves distally, it carries syringe assembly 22 distally and moves it back to the retracted position. Spring 66 biases the retraction mechanism 26 distally and thereby maintains syringe assembly 22 in its retracted position after an injection event. A locking mechanism such as a detent on the shuttle assembly 60 and a recess on the housing 38 member may additionally provide a locking engagement to secure syringe assembly 22 in the retracted position with needle 34 disposed within housing 38 after an injection event whereby the user may then dispose or otherwise handle device 20 in a safe manner.

Although FIGS. 1-3 depict and describe an exemplary drive mechanism 24 and an exemplary retraction mechanism 26, other mechanisms may also be used to drive syringe assembly 22 from the storage position to the injection position, and/or from the injection position to the retracted position. Such drive and/or retraction mechanisms may (but need not) include one or more springs or deformable parts that store energy when they are held in a pre-triggered state and, when triggered, release said stored energy to drive the syringe assembly from the storage position to the injection position, and/or from the injection position to the retracted position. Such mechanisms may (but need not) include mechanisms that generate motive force using chemical reactions or processes, e.g., by generating gas through the mixture of two or more reagents, or by igniting a small amount of combustible or explosive material. Such chemically-driven mechanisms may comprise one or more storage containers for the chemical reagents, a trigger that punctures or opens said storage containers, allows said reagents to mix, and/or which provides a spark or other ignition source for beginning the chemical reaction, and a movable piston or other component that moves in response to increasing gas pressure generated by the resulting chemical reaction. Such mechanisms may (but need not) include mechanisms that use stored electrical power (e.g., in a battery) to run electric motors that drive and/or retract the syringe assembly, or to trigger other physical or chemical mechanisms. Such mechanisms may (but need not) include hydraulic or pneumatic systems (e.g., tubes), gears, cables, pulleys, or other known components for transferring kinetic energy from one component to another. In some embodiments, rather than having separate mechanisms for driving the syringe assembly and then retracting the syringe assembly, a single mechanism may be configured to both drive and then retract the syringe assembly.

Figure 4:
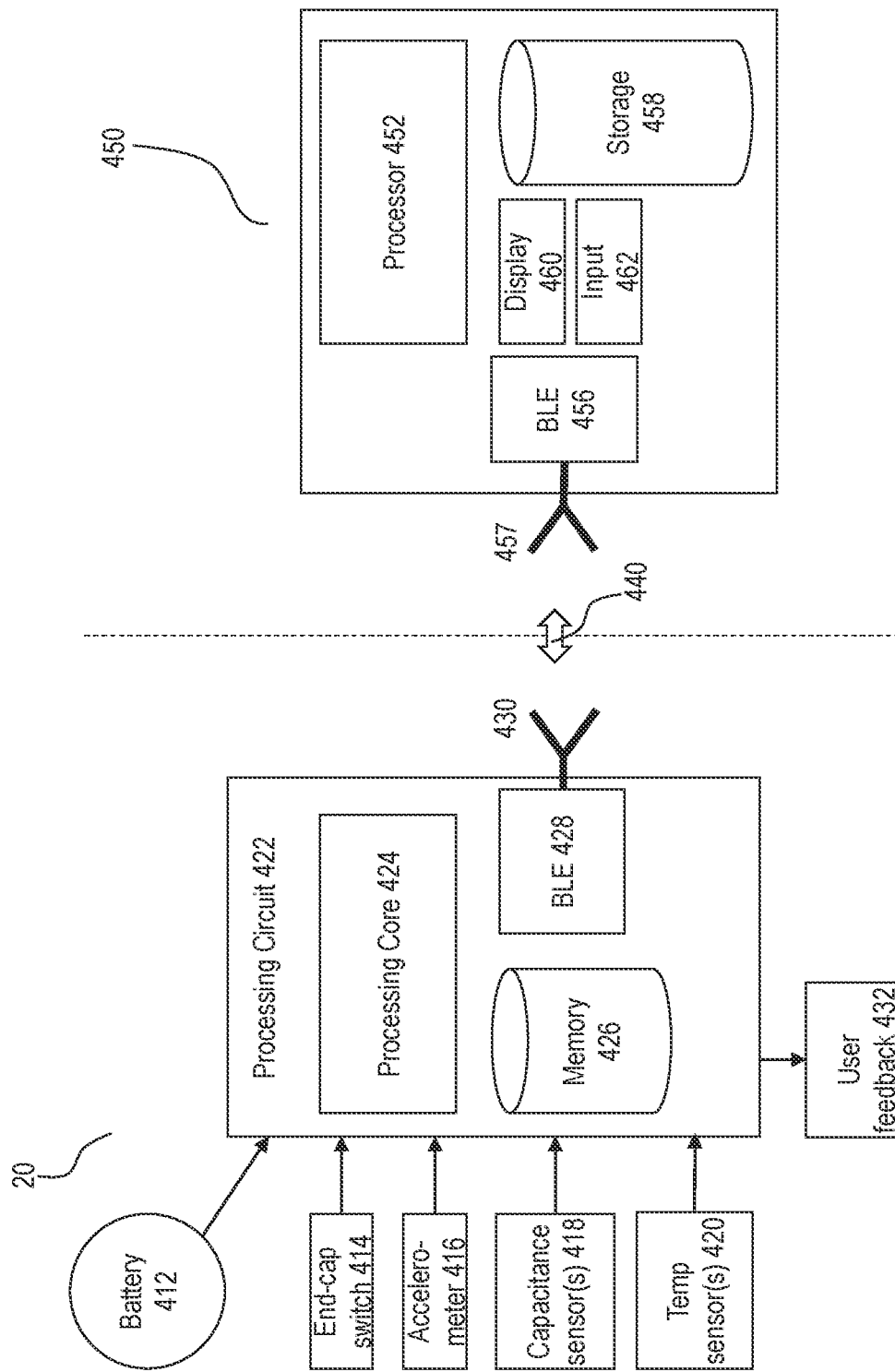
FIG. 4 is a system architecture view of electrical components within the injection device and an exemplary external computing device.

FIG. 4 provides a system architecture view of electrical components within device 20, as well as a communication link with an exemplary external device 450, according to some embodiments. Device 20 may comprise a processing circuit 422 mounted on or within housing 38. Processing circuit 422 may be powered by a power source 412 (e.g., a battery) and may comprise a processing core 424 and a memory 426. Memory 426 may store logic that, when executed by the processing core 424, causes the processing circuit 422 to perform the operations described herein. Memory 426 is any suitable computer readable medium that is accessible by processing core 424. Memory 426 may be a single storage device or multiple storage devices, may be located internally or externally to processor core 424, and may include both volatile and non-volatile media. Exemplary memory 426 includes random-access memory (RAM), read-only memory (ROM), electrically erasable programmable ROM (EEPROM), flash memory, a magnetic storage device, optical disk storage, or any other suitable medium which is configured to store data and which is accessible by processor core 424, whether directly or indirectly via one or more intermediary devices or wired or wireless communication links. The term "logic", "control logic", "instructions", or "application" as used herein may include software and/or firmware configured to execute on one or more programmable processors, field-programmable gate arrays (FPGAs), and/or digital signal processors (DSPs), or any combination of the foregoing. Alternatively, or in addition, "logic", "control logic", "instructions" or "application" may comprise hardwired logic (e.g., Application Specific Integrated Circuits (ASICs)) configured to implement the functions described herein. Therefore, in accordance with the embodiments, various logic may be implemented in any appropriate fashion and would remain in accordance with the embodiments herein disclosed.

Processing circuit 422 may also be communicatively coupled with a plurality of sensors, such as end-cap switch(es) 414 for detecting whether end-cap 36 is attached to device 20 or not, accelerometer(s) 416 for detecting at least one of an orientation, movement, and/or acceleration of device 20, capacitance sensor(s) 418 for detecting contact with skin tissue, and/or temperature sensor(s) 420 for detecting at least one of an ambient temperature and a temperature of device 20. Processing circuit 422 may also be connected to a device 432 for providing user feedback that is integrated with device 20. The means for user feedback may include one or more indicator lights (e.g., implemented using light-emitting diodes (LEDs)), a display, a haptic indicator such as a vibration motor, and/or an auditory indicator such as a speaker. Processing circuit 422 may be communicatively coupled with each of the aforementioned components via one or more physical, electrical channels, such as (but not limited to) a General-Purpose Input/Output (GPIO) pin, an Inter-Integrated Circuit (I2C) bus, a Serial Peripheral Interface (SPI) connection, a Universal Asynchronous Receiver/Transmitter (UART) connection, and/or a Controller Area Network (CAN) bus. In some cases, signals received by the processing circuit 422 from some or all of the sensors may also be converted from an analog to a digital signal using an analog-to-digital converter (ADC), not shown. In some embodiments, processing circuit 422 may take the form of a System on Chip (SOC) integrated circuit. In some embodiments, processing circuit 422 may also be implemented using other types of components, such as a microcontroller (MCU), or an Application Specific Integrated Circuit (ASIC).

Processing circuit 422 may also be configured to allow injection device 20 to communicate wirelessly with an external device, such as for example, a mobile phone, a wearable device, a laptop, and/or a server database. To facilitate wireless communication, processing circuit 422 may comprise a Bluetooth Low Energy (BLE) circuit 428 communicatively coupled with a BLE antenna 430. BLE circuit 428 and BLE antenna 430 allow processing circuit 422 to establish a wireless BLE communication link 440 with external device 450. Wireless BLE communication link 440 may transfer data in one direction only (e.g., from delivery device 20 to external device 450) or in two directions. Wireless link 440 may be a BLE wireless communication session established after a Bluetooth handshake or pairing process, or it may comprise transmission of data prior to or without any handshake or pairing process. Although the embodiment depicted in FIG. 4 depicts a BLE circuit and antenna, any suitable wireless communication standard may be used.

FIG. 4 also shows an exemplary external computing device 450 that is physically separate from injection device 20. In this embodiment, exemplary external device 450 may take the form of a mobile smartphone. Alternatively, any suitable computing device may be used, including but not limited to a smartwatch, laptop, desktop, tablet, or server computer, for example. External device 450 may comprise a processor 452 (e.g., a microprocessor or CPU) and storage 458. Storage 458 may comprise non-transitory computer-readable media storing computer-executable instructions that, when executed by processor 452, causes device 450 to perform the operations described herein. These computer-executable instructions may comprise a mobile application, such as a medical mobile application. Device 450 may further comprise a display 460 and a user input device 462. User input device 462 may comprise physical buttons, switches, or other types of input devices integrated with or communicably coupled to device 450, such as a keyboard, keypad, microphone, mouse pointer, or other suitable user input device. Although depicted separately in FIG. 4, all or a portion of user input device 462 may be integrated with display 460, e.g., in a touch-sensitive screen operative to display data and receive user inputs. Device 450 may be configured to establish a wireless communication link 440 with injection device 20. For example, external device 450 may include a BLE circuit 456 communicatively coupled with BLE antenna 457 which communicates with processing circuit 422 in device 20 via communication link 440.

As described herein, the medication delivery device 20 may be configured to generate data about a state of the device 20 and/or about the occurrence of a certain event or action. For example, a processing circuit of the medication delivery device may analyze a signal from an accelerometer to determine when an injection event has been initiated and/or completed. As another example, the processing circuit may analyze a signal from a skin contact sensor to verify proper contact with the user's skin prior to and/or during the initiation of an injection event. In some embodiments, the generated data is provided to external device 450, such that the external device 450 can be used to monitor injection event activity and/or the condition of the medication delivery device. In some embodiments, the data generated by device 20 and provided to external device 450 may include information about the time of an injection event, the time that has elapsed since an injection event, the date of injection event, the temperature of a medication stored in the medication delivery device, the state of the skin contact sensors, or any other suitable data, as aspects of the techniques described herein are not limited in this respect. A mobile application on the computing device may be used to log data (e.g., injection event information) received from the medication delivery device, such as the time and/or date of an injection event. In some embodiments, this may help a user to adhere to an injection regimen, since the injection event information is automatically and accurately logged.

The exemplary electrical components in FIG. 4 may be modified in several ways in different embodiments. For example, in some embodiments, some of the sensors 414, 416, 418, and 420 may be omitted. Other sensors in addition to sensors 414, 416, 418, and 420 may be connected to processing circuit 422, such as one or more micro-switch sensors for detecting movement or position of various components within device 20, an ambient light sensor for detecting the presence, absence, and/or intensity of ambient light, and/or a magnetometer for detecting movement or positions of various components within device 20 (e.g., of plunger 44). Device 20 may also omit user feedback 432 in some embodiments. In some embodiments, in addition to or as an alternative to BLE circuit 428 and BLE antenna 430, processing circuit 422 may comprise or be connected to other types of wireless communication circuits, such as a RFID circuit and/or antenna, or a NFC circuit and/or antenna.

As previously discussed, processing circuit 422 may be mounted anywhere on or within housing 38 of device 20. For example, processing circuit 422 may be mounted near the distal end of device 20, within, surrounding, or directly proximal to button 52. Processing circuit may be placed anywhere along the length of user-graspable portion 37 of housing 38. In some embodiments, processing circuit 422 may be embedded within housing 38; in other embodiments, processing circuit 422 may be releasably or permanently attached to the exterior of housing 38.

Figure 5:
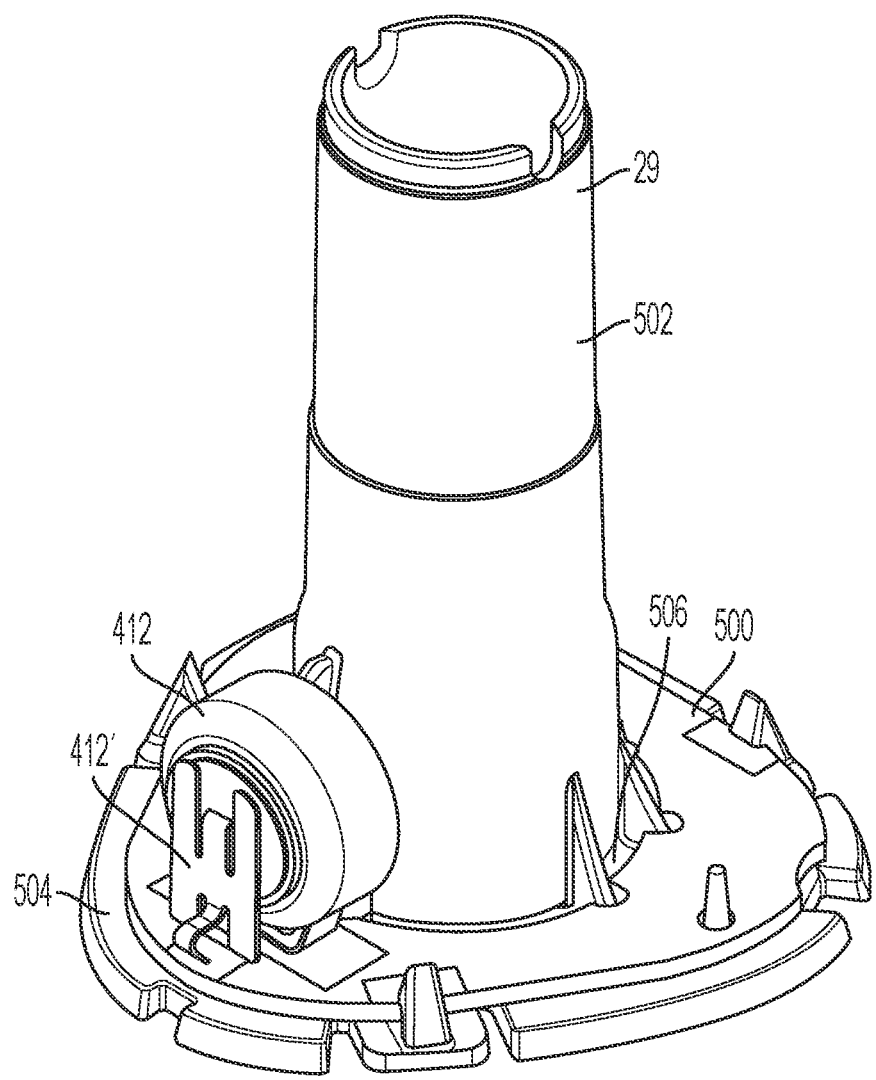
FIG. 5 is a perspective view of a lower body support member supporting a printed circuit board (PCB) in the injection device.
Figure 6A:
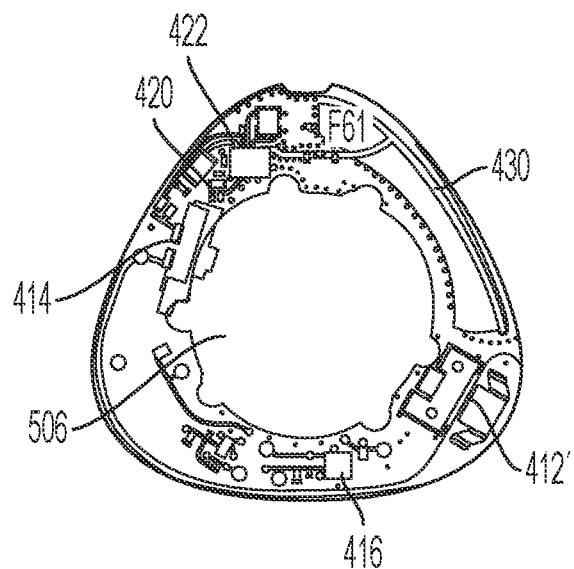
FIGS. 6A and 6B are top and bottom views of the PCB, respectively.
Figure 6B:
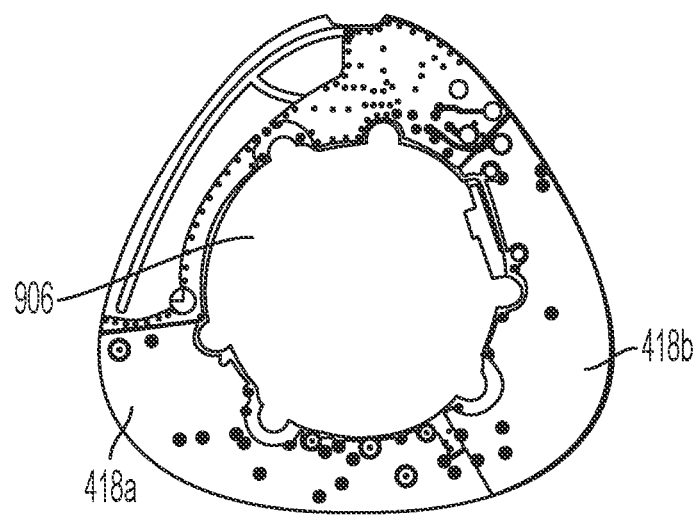

In some embodiments, processing circuit 422 may be mounted on lower body support member 29 adjacent to the proximal end of device 20, in the outwardly-flared end portion 39 adjacent the proximal opening 40. FIGS. 5, 6A, and 6B depict one such embodiment, in which processing circuit 422 is mounted on a printed circuit board (PCB) 500 disposed on lower body support member 29. As depicted in FIG. 5, lower body support member 29 comprises a hollow and substantially cylindrical-shaped body 502 that surrounds needle 34 (depicted in FIGS. 1-3). Cylindrical body 502 is mounted on a proximal plate 504 that, in this embodiment, has a trilobular shape. Both body 502 and 504 may be formed from any suitable rigid material, such as a rigid polymer or metal. Body 502 and 504 may be manufactured separately then bonded together using any suitable bonding method, including screws, adhesive, pressure fit, ultrasonic welding, or other suitable technique. Alternatively, body 502 and 504 may be manufactured as a single monolithic component. PCB 500 may be mounted on a distal surface of proximal plate 504. PCB 500 may be shaped substantially similarly to proximal plate 504 (e.g., in this embodiment, taking on the shape of a trilobular plate) so as to cover a majority of the distal surface of plate 504. PCB 500 may also define a lumen 506 configured to receive cylindrical body 502 therethrough.

FIG. 6A depicts a view of the distal side of PCB 500 while FIG. 6B depicts a view of the proximal side of PCB 500. As shown, PCB 500 may comprise a battery clip and/or contact 412' configured to receive and draw power from battery 412. PCB 500 may further comprise BLE antenna 430 configured to communicate wirelessly with a remote device (e.g., device 450) as described herein. PCB 500 may further comprise processing circuit 422, as well as a temperature sensor 420 and user feedback device 432 (not shown in FIG. 6A, 6B), as described herein. PCB 500 may also comprise an end cap switch 414 configured to detect whether end cap 36 is attached to the proximal end of device 20, as described herein. In some embodiments, end cap switch 414 may take the form of a physical switch that, when end cap 36 is attached, is biased by end cap 36 or one or more intermediate deformable members in contact with end cap 36, into a first state. When end cap 36 is detached, end cap switch 414 may be biased into a second state. The end cap switch 414 may output different electrical signals depending on whether it is in the first state or the second state. These signals may be provided to processing circuit 422 to allow the processing circuit to determine whether end cap 36 is attached or not.

The proximal side of PCB 500 further comprises two capacitive touch pads 418a and 418b (collectively referred to as 418), as described herein. Capacitive touch pads 418 may be configured to detect whether touch pads 418 are placed in contact or in proximity with skin tissue based on measured capacitance. Specifically, such capacitance sensors may be configured to detect proximity of human tissue (e.g., skin tissue) by detecting such tissue's effect on an electric field created by the sensor (e.g., by detecting the effect of such tissue on the capacitance of a circuit being monitored or measured by the sensor). Capacitance sensors do not require a metallic, electrical terminal that directly contacts tissue, and so may be partially or completely sealed behind a protective, non-conductive cover (e.g., made of plastic).

The distal side of PCB 500 further comprises an accelerometer 416. Accelerometer 416 may detect shocks or accelerations caused by initiation of a dispensing event in which syringe assembly 22 is driven by drive mechanism 24 from the storage position to the injection position. Accelerometer 416 may also detect shocks or accelerations caused by a retraction movement upon completion of the dispensing event in which syringe assembly 22 is driven by the retraction mechanism 26 from the injection position to the retracted position. Accelerometer 416 may send an output signal to processing circuit 422 via one or more electrical connections to allow processing circuit to analyze the output signal.

In some embodiments, processing circuit 422 may analyze the signal output from accelerometer 416 to determine a certain condition or state of the device 20, or to detect the occurrence of a certain event or action. For example, processing circuit 422 may be configured to determine when a dispensing event is initiated or completed based on signals from accelerometer 416, either alone or in conjunction with signals from other sensors (e.g., the capacitive skin contact sensors 418). Methods for determining when a dispensing event has been initiated or completed are described in further detail in U.S. Patent App. Pub. No. 2021/0093784 A1 published Apr. 1, 2021 to Adams et al., the entire disclosure of each of which is hereby incorporated herein by reference.

When a dispensing event is initiated, drive mechanism 24 is activated to drive the syringe assembly 22 from the storage position to the injection position. This driving motion imparts one or more accelerations that may be detected in the signal output from accelerometer 416. For example, the pushing force imparted by drive mechanism 24 as it drives syringe assembly 22 from the storage position in the proximal direction may cause accelerometer 416 to detect an acceleration in the distal direction along longitudinal axis 48. When syringe assembly 22 hits its stopping position at its injection position at the end of this driving motion, the sudden stop of syringe assembly 22 may cause accelerometer 416 to detect an acceleration in the proximal direction along longitudinal axis 48. Either this proximal or distal acceleration (or both) may cause accelerometer 416 to output a first acceleration spike that may be detected by processing circuit 422. This first acceleration spike may be indicative of initiation of a dispensing event.

Similarly, when a dispensing event has been completed, the retraction mechanism 26 is activated to drive the syringe assembly 22 from the injection position to the retracted position. This driving motion imparts one or more accelerations that may also be detected in the signal output from accelerometer 416. For example, the pushing force imparted by retraction mechanism 26 as it drives syringe assembly 22 from the injection position in the distal direction may cause accelerometer 416 to detect an acceleration in the proximal direction along longitudinal axis 48. When syringe assembly 22 reaches the retracted position, the sudden stop of syringe assembly 22 may cause accelerometer 416 to detect an acceleration in the distal direction along longitudinal axis 48. Either this proximal or distal acceleration (or both) may cause accelerometer 416 to output a second acceleration spike that may be detected by processing circuit 416. This second acceleration spike may be indicative of completion of the dispensing event. As used herein, an "acceleration spike" is defined as any artifact in an acceleration or vibration signal output by an accelerometer or vibration sensor (e.g., a piezo sensor) that is indicative of initiation and/or completion of a dispensing event. When (or after) processing circuit 422 detects the initiation and/or completion of a dispensing event, processing circuit 422 may send injection event information to external device 450. As previously described herein, such injection event information may include the time of an injection event, the time that has elapsed since an injection event, the date of an injection event, the temperature of a medication stored in the medication delivery device, the state of the skin contact sensors, or any other suitable data.

Device 20 may be used to deliver an injection of stored medication to any suitable injection site on the patient's body, such as the patient's left or right abdomen, left or right thigh, left or right buttock, or the underside of the patient's left or right upper arm. However, depending on the physiology of the patient's body, the inventors have appreciated that injecting at some injection sites may lead to less injection site pain at the time of injection than other injection sites. Also depending on the physiology of the patient's body, some injection sites may lead to less injection site pain in the minutes and hours following the injection than other injection sites, e.g., due to a lower inflammatory or other injection response at the injection site. It would therefore be desirable to provide guidance to the user and/or the patient regarding which injection sites may lead to less pain.

The inventors have also appreciated that capacitive touch pads 418 on device 20 may be used to gather data regarding the physiology of different injection sites on the patient's body. Such data may be used by device 20 and/or external device 450 to provide insight to a user regarding a level of pain that would be expected to be experienced by the patient from a potential injection at different injection sites. Generally, injections at injection sites having greater fat content are expected to be less painful for the patient, both at the time of injection and in the minutes and hours following the injection, compared to injection sites having less fat content. Furthermore, injection sites having greater fat content are expected to have lower capacitance compared to injection sites having less fat content when measured by capacitive touch pads 418. This is because injection sites having greater fat content are expected to have lower water content (and thus, lower capacitance) compared to injection sites having lower fat content.

Figure 7:
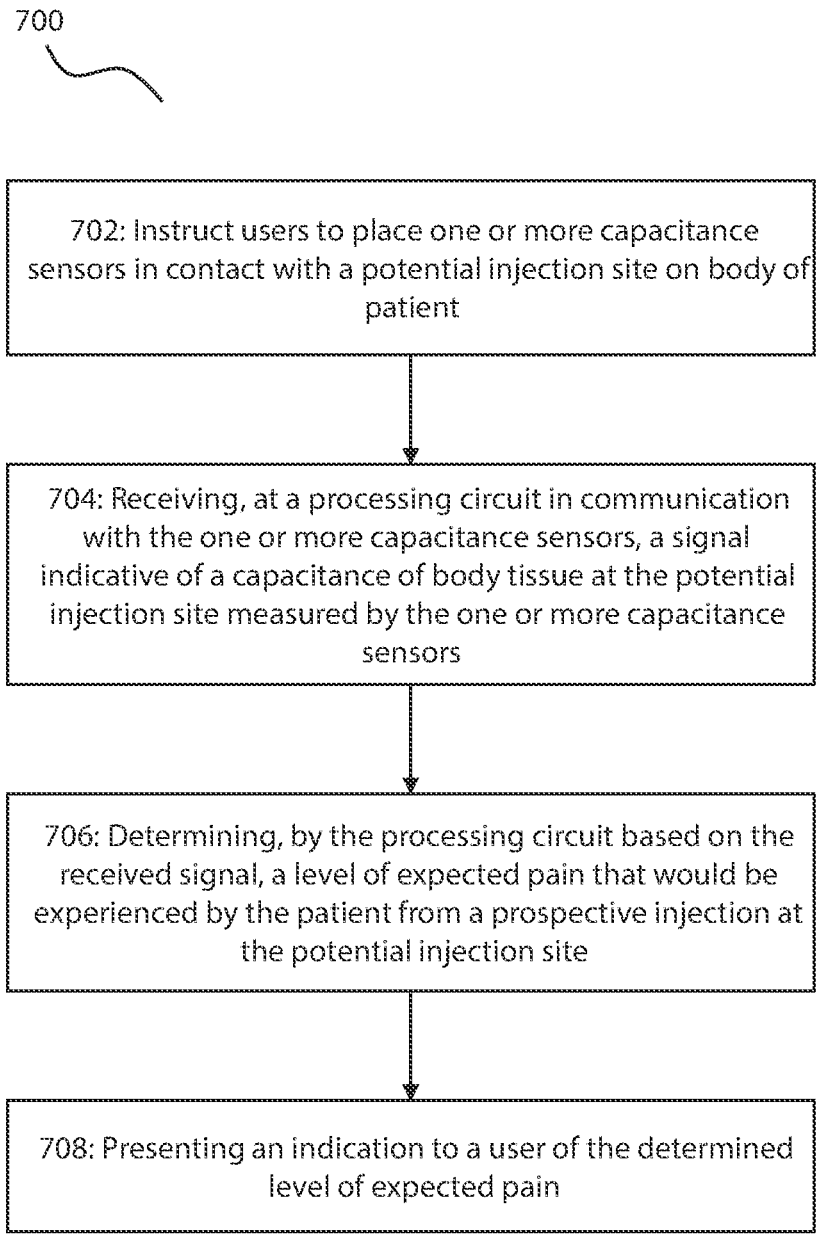
FIG. 7 is a flowchart depicting exemplary logic for evaluating injection sites on a body of the patient using capacitive data gathered by capacitance sensors.

FIG. 7 presents exemplary logic 700 for evaluating injection sites on a body of a patient using capacitive data gathered by capacitive sensors, according to some embodiments. At step 702, the user is instructed to place one or more capacitance sensors in contact with a potential injection site on the body of the patient (e.g., the right thigh). For example, these instructions may be provided to the user using display 460 of external device 450. Exemplary processes/methods for so instructing the user are described in greater detail below, for example, in FIG. 8 and FIGS. 10A-10K. In some embodiments, these capacitance touch pads may be capacitance touch pads 418 on an injection device such as device 20. In other embodiments, other types of capacitance sensors may be used, whether or not coupled to a drug-delivery device.

At step 704, a processing circuit in communication with the one or more capacitance sensors may receive a signal indicative of a capacitance of body tissue at the potential injection site measured by the one or more capacitance sensors. This processing circuit may be processor 452 at external device 450 but may also be processing circuit 422 at device 20.

At step 706, the processing circuit determines, based on the received signal, a level of expected pain that would be experienced by the patient from a prospective injection at the potential injection site. In general, a lower capacitance may be associated with a lower level of expected injection site pain, as lower capacitance indicates lesser water content, which is indicative of greater fat content at the injection site. Conversely, a higher capacitance may be associated with a higher level of expected injection site pain. The level of pain may be determined in different ways. In some embodiments, the level of pain may be a categorization of an injection site into one of two pain levels (e.g., "low" pain or "high" pain), three pain levels (e.g., "low", "medium", or "high" pain), or more pain levels (any number of pain levels may be used). In such embodiments, the level of pain may be determined by comparing the measured capacitance against one or more pre-programmed thresholds which delineate the capacitance boundaries between each injection site pain level. In some embodiments, the level of expected pain may be a numerical score or value along a range of values. In such embodiments, the level of expected pain may be generated by comparing the measured capacitance against a range of expected capacitance values for different injection sites on the average human body—the determined level of expected pain may comprise an indication of where the measured capacitance falls in the expected range.

In some embodiments, the determined level of expected pain may be saved into memory (e.g., storage 458 or memory 426) for later analysis or presentation. This determined level of expected pain may also be transmitted to other devices over a wired or wireless communication link for storage or further analysis. For example, the generated indication may be transmitted, whether directly or via one or more optional intermediary components, to a desktop or laptop computer for storage or analysis, and/or transmitted over a network to a remote server for storage or analysis.

In some embodiments, the determined level of expected pain may also be optionally presented to a user for viewing. For example, at step 708, the processing circuit generates and presents an indication to a user of the determined level of expected pain. This generated indication may be presented to the user using any of the previously described user feedback devices 432 integrated with device 20. As one illustrative embodiment, device 20 may comprise an array of LEDs, wherein each LED in the array corresponds to a different injection site. The generated indication may be presented to the user by lighting up each LED in the array with different colors, intensities, durations, and/or patterns indicative of the expected level of pain associated with each injection site. In another embodiment, device 20 may comprise a single LED that lights up with different colors, intensities, durations, and/or patterns depending on the expected level of pain associated with a single injection site, e.g., the injection site most recently measured or currently being measured by capacitance touchpads 418 on device 20. Alternatively, or in addition, device 20 may be provided with a small speaker for providing audible messages to a user, including the aforementioned generated indication. In some embodiments, alternatively, or in addition, this generated indication may be presented to the user via display 460 on external device 450. Some examples of logic for presenting such generated indications on external device 450 is described below in relation to FIGS. 8 and 9.

Figure 8:
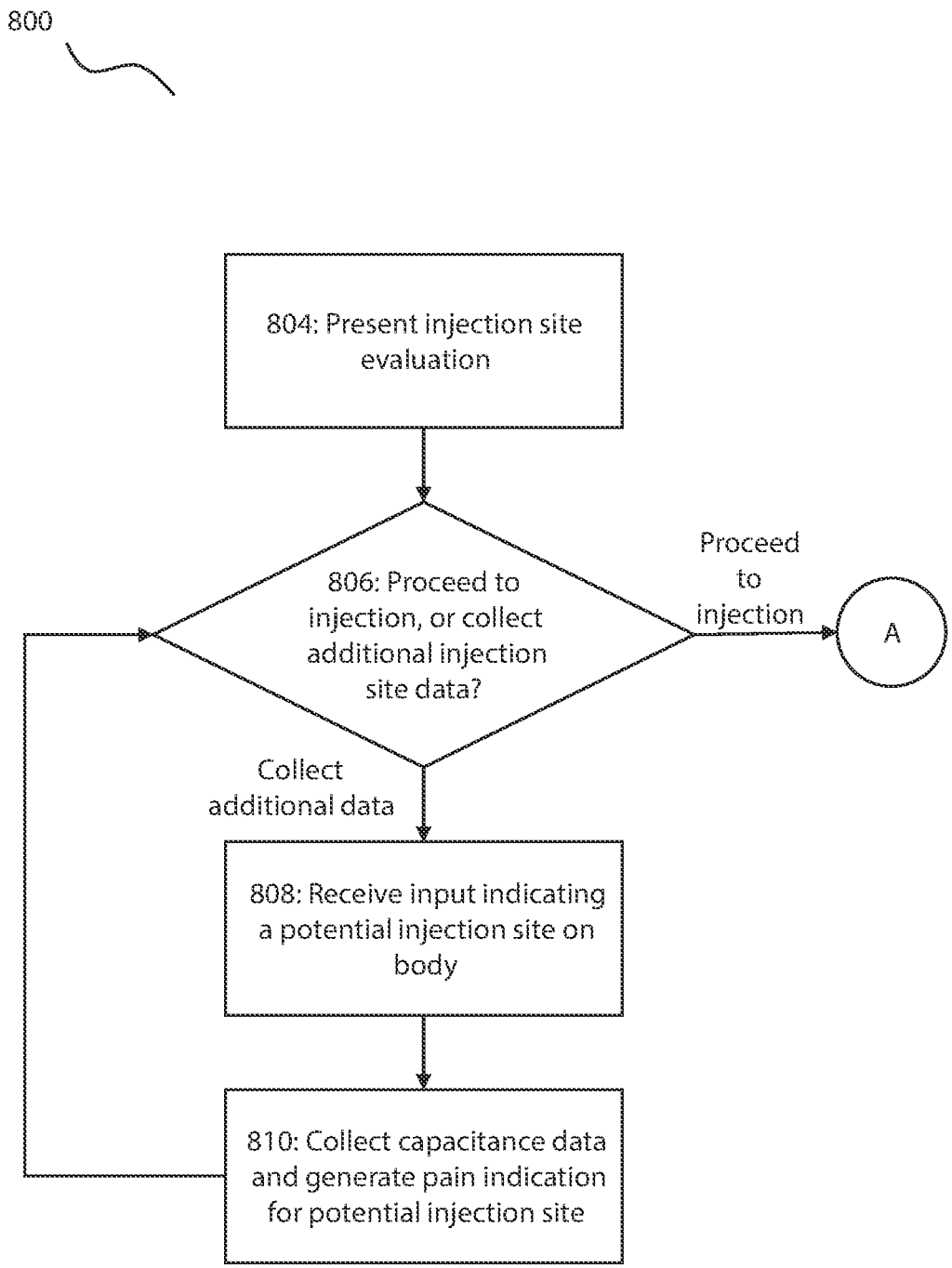
FIG. 8 is a flowchart depicting exemplary logic for gathering capacitance data and generating insights regarding potential injection site pain.

FIG. 8 depicts an exemplary logic 800 for gathering capacitance data and generating insights regarding potential injection site pain, according to some embodiments. For ease of explanation, logic 800 shall be described herein as being implemented by external device 450 based on data received from the capacitance sensors 418 from device 20. However, it should be appreciated that logic 800 may also be implemented solely on device 20 in embodiments where device 20 is equipped with a user interface and/or user input devices (e.g., a display and buttons, or touch-sensitive display) suitable for communicating the described data and screenshots to the user. In some embodiments, certain parts of logic 800 may be implemented by external device 450 while other parts may be implemented by processing circuit 422 on device 20, such that device 450 and device 20 cooperatively implement logic 800.

When the user launches logic 800 (e.g., by launching a mobile application on external device 450, or by initiating a feature in such mobile application), external device 450 begins by presenting an initial injection site evaluation (step 804). This evaluation may comprise initial guidance comparing, for different potential injection sites, the level of injection site pain that would be expected to be experienced by the patient upon injection. For example, this evaluation may comprise a score, color, or other indicator of expected injection site pain for different injection sites on the patient's body. This evaluation may also comprise a rank ordering of injection sites on the patient's body, from most-to-least or from least-to-most painful.

If the user has never launched logic 800 before, such initial guidance may be based on pre-programmed parameters for an "average" patient, informed by the results of experiments on or experiences of a population of patients, but not based on any physiological data gathered for the specific patient being injected. If the user has launched logic 800 before, such initial guidance may be alternatively or additionally based on previously measured or collected data for the specific patient being injected. In some embodiments, if no pre-programmed parameters for an "average" patient has been provided and no previously-recorded data for the patient to be injected is available, the injection site evaluation presented at step 804 may be a null or unpopulated evaluation.

Figure 10A:
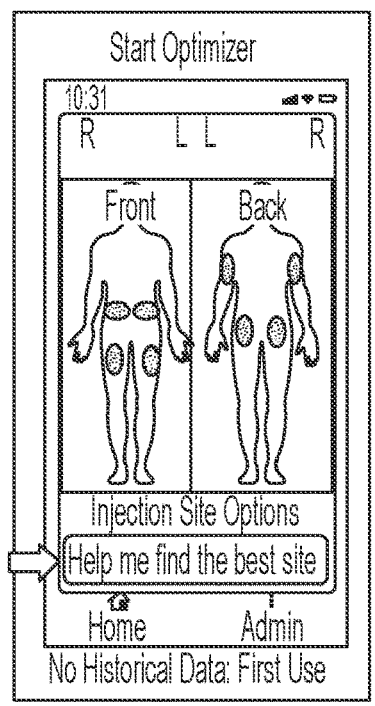
FIGS. 10A-K present exemplary screenshots displayed on the external computing device.

FIG. 10A provides an exemplary screenshot for an initial injection site evaluation provided at step 804. FIG. 10A depicts diagrams of the front and back of a human body on the left and right side of the screen, respectively. Potential injection sites are highlighted on the diagrams using ovals. In this embodiment, the following injection sites are highlighted: left and right abdomen, left and right thigh, left and right buttock, and the underside of the left and right upper arm. In this embodiment, since no data is available for either an "average" patient or for the particular patient being injected, all the ovals are colored grey to indicate that no data is available.

Logic 800 continues at step 806, where the external device 450 waits for user input regarding whether to proceed to injection, or to collect additional injection site data. If the external device 450 receives user input indicating "proceed to injection", logic branches to logic 900, discussed with respect to FIG. 9. If the external device 450 receives user input indicating that the user desires to collect additional injection site data, logic 800 branches to step 808.

Figure 10B:
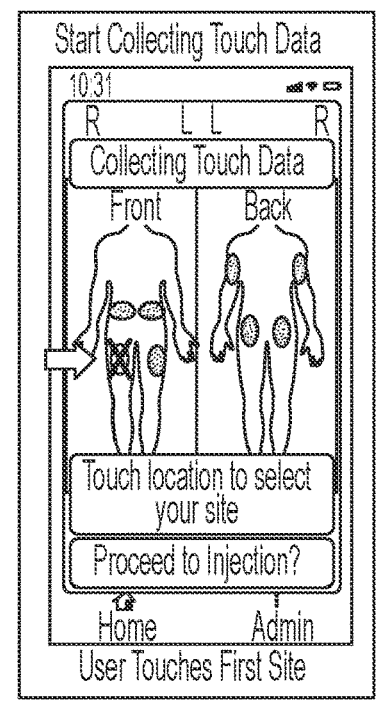

At step 808, external device 450 receives input from the user indicating a potential injection site on the patient's body that the user would like to collect data on. FIG. 10B provides an exemplary screenshot for this step. In this example, FIG. 10B may be reached from the screenshot at FIG. 10A when the user presses the button "Help me find the best site". Once at FIG. 10B, the user may press "Proceed to Injection" if the user desires to branch to logic 900. However, if the user desires to branch to step 808, the user may indicate a potential injection site on the patient's body by touching one of the indicated injection sites on the depicted body diagrams. In this embodiment, the user has selected the injection site corresponding to the patient's right thigh. Once the user touches that injection site, the injection site on the body diagram's right thigh changes appearance (as indicated by the symbol "X") to indicate that that injection site has been selected.

At step 810, external device 450 and device 20 work together to collect capacitance data and generate a pain indication for the selected potential injection site. For example, the user may place capacitance touch pads 418 on device 20 against the selected injection site (in this example, the right thigh). Processing circuit 422 on device 20 may read and record capacitance values measured by touch pads 418 during this touch, then transmit the recorded values to external device 450 to generate a pain indication, as previously described in relation to FIG. 7. If needed, the user may be directed to lift off and set down device 20 on the selected potential injection site several times so that device 20 may read, record, and transmit multiple recorded capacitance values to external device 450—multiple readings may make the resultant generated pain indications more accurate. If multiple readings are taken, these readings may be averaged to generate an aggregate capacitance reading, which may in turn be used to generate an overall pain indication for that injection site. Once external device 450 has received sufficient capacitance data to generate a pain indication for the selected injection site, the selected injection site may change appearance again (as indicated by the darkened color for the right thigh in FIG. 10C) to indicate that sufficient data has been collected.

After collecting sufficient capacitance data for the selected injection site, logic 800 branches back to step 806 where the user is again presented with the option to proceed to injection or to collect additional injection site data. In FIG. 10C, if the user selects the button "Proceed to Injection?", logic 800 will branch to logic 900 in FIG. 9. However, if the user selects "Continue Touch Data?", logic 800 will branch back to step 808.

Figure 9:
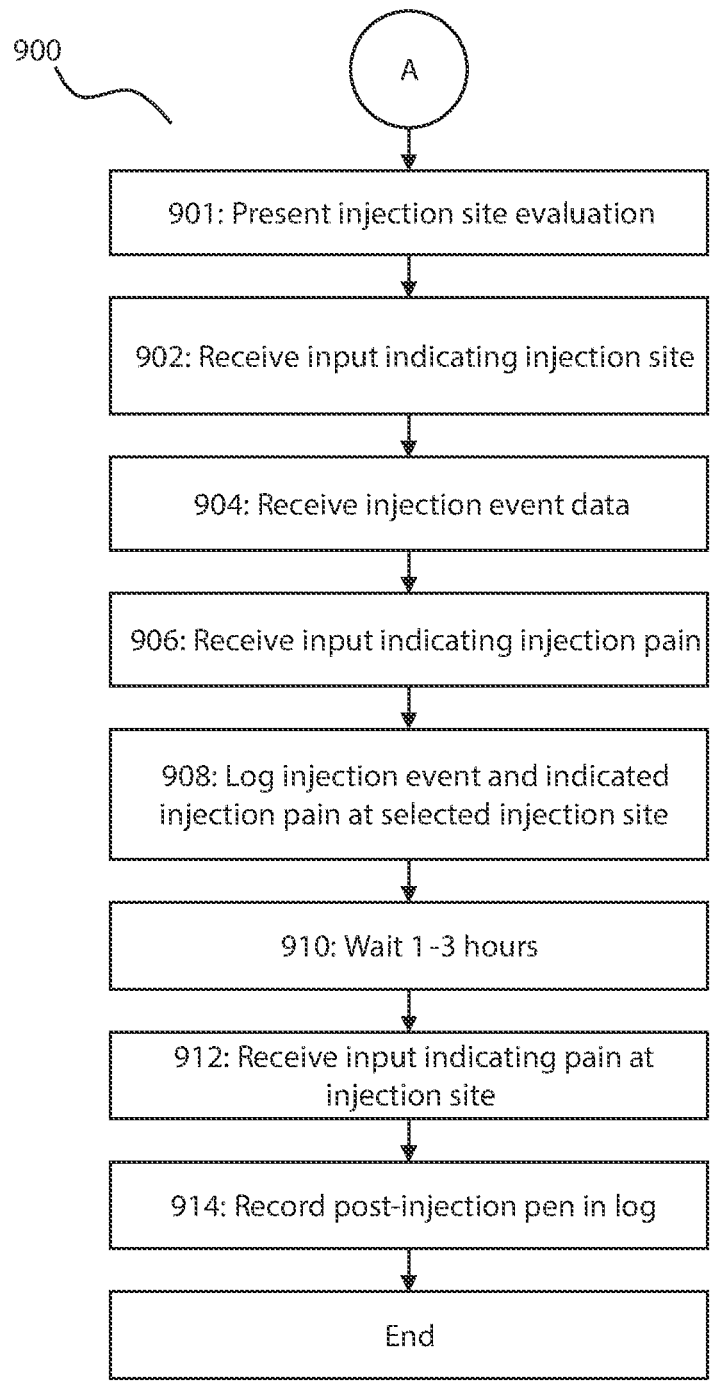
FIG. 9 is a flowchart depicting exemplary logic for viewing generated insights, and recording/logging injection data.
Figure 10C:
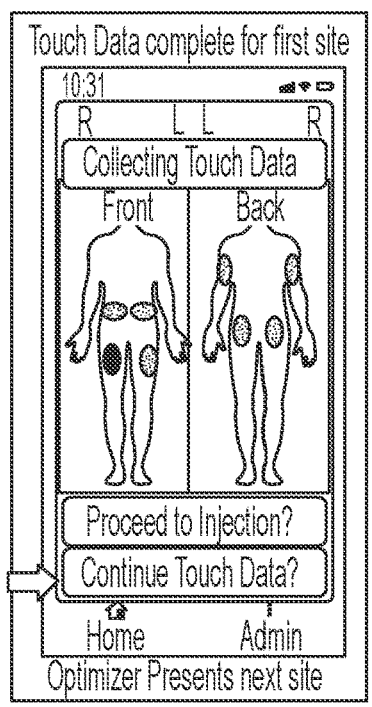
Figure 10D:
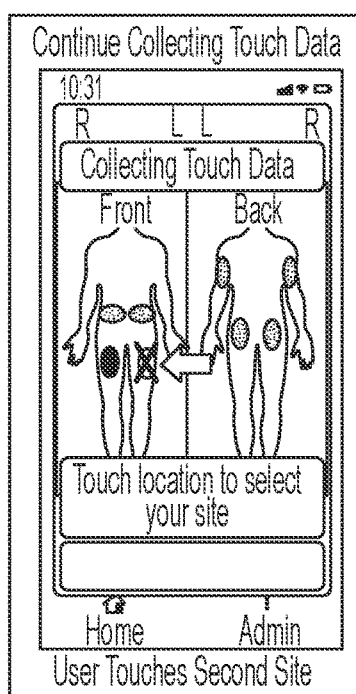
Figure 10E:
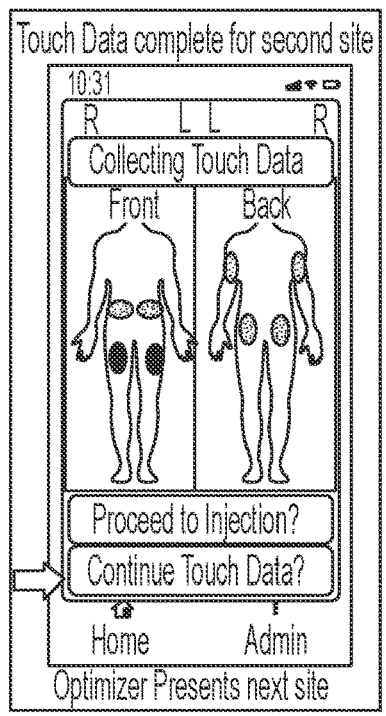

In the example depicted in FIG. 10C, the user selects "Continue Touch Data?", which brings the user to the exemplary screenshot depicted in FIG. 10D (and back to step 808 in logic 800). Here, the user is again presented with diagrams of the front and back of the human body, with injection sites highlighted. This time, however, since data has already been collected for the right thigh, the injection site for the right thigh is colored differently than other injection sites to indicate that this is the case. The user selects another injection site (in this example, the left thigh) to collect data on. After selecting the left thigh, the user again places the capacitance pads 418 on device 20 against the selected injection site (left thigh, as indicated by the "X" symbol) to collect capacitance data. When sufficient data on the left thigh injection site has been collected, the injection site on the left thigh changes appearance, as depicted in FIG. 10E. After collecting data on the left thigh, the user is again presented with an option to "Proceed to Injection?" (which would take the user to logic 900 in FIG. 9) or to "Continue Touch Data?" (which would take the user again to step 808).

Figure 10F:
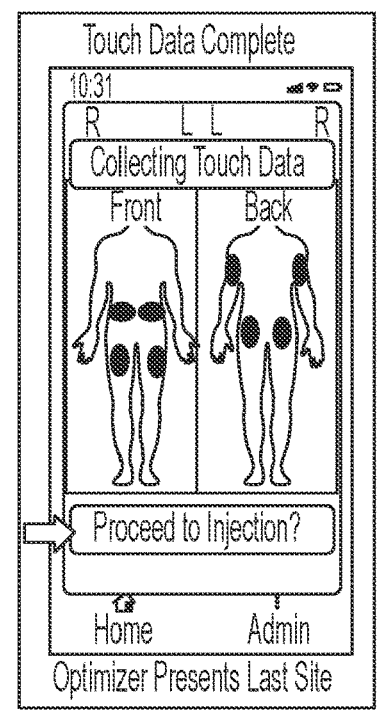

The user thus cycles through steps 806, 808, and 810 indefinitely until either the user has finished collecting data for all available injection sites or the user selects "Proceed to Injection." FIG. 10F depicts an exemplary screenshot in which the user has finished collecting data for all eight depicted injection sites. In this screenshot, since data has been collected for all injection sites, there is no longer any option to "Continue Touch Data?" Instead, the user is presented with an option to press the button labeled "Proceed to Injection?"

When the user presses the "Proceed to Injection" button, logic 800 branches to logic 900 in FIG. 9. At step 901, external device 450 presents an evaluation of different injection sites on the user's body based on the previously collected capacitance data. This step may be similar to the evaluation presented at step 804. As described previously, this evaluation may comprise a score, color, or other indicator of expected injection site pain for different injection sites on the patient's body. This evaluation may also comprise a rank ordering of injection sites on the patient's body, from most-to-least or from least-to-most painful.

Figure 10G:
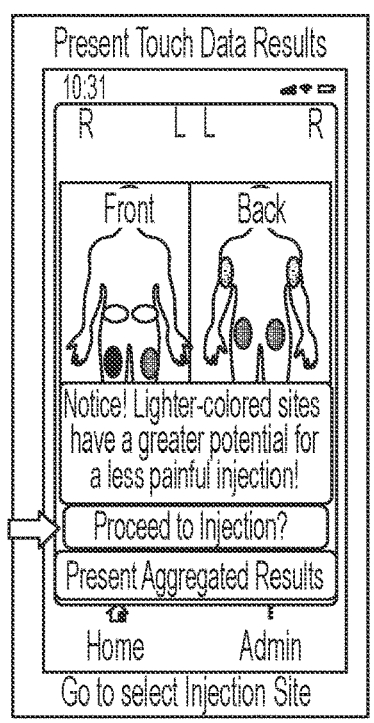

FIG. 10G provides an exemplary screenshot for the injection site evaluation provided at step 901. FIG. 10G may be similar in appearance to FIG. 10A, except that since capacitance data has now been collected for each injection site on the patient's body, each injection site has been filled in with a color indicative of the level of expected injection site pain for that site. In this example, lighter colored injection sites are expected to exhibit relatively lower injection site pain, sites colored medium gray are expected to exhibit a medium level of injection site pain, and sites colored dark gray or black are expected to exhibit a relatively high level of injection site pain. In general, any color scheme may be used to indicate expected injection site pain. The level of expected injection site pain may be generated from the collected capacitance data using any of the techniques previously-described in relation to FIG. 7.

Figure 10H:
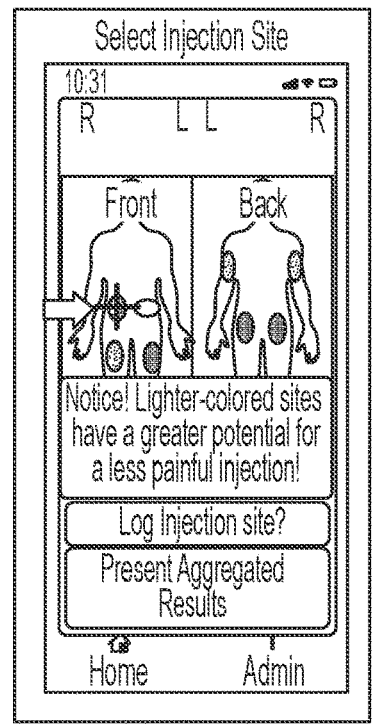
Figure 10I:
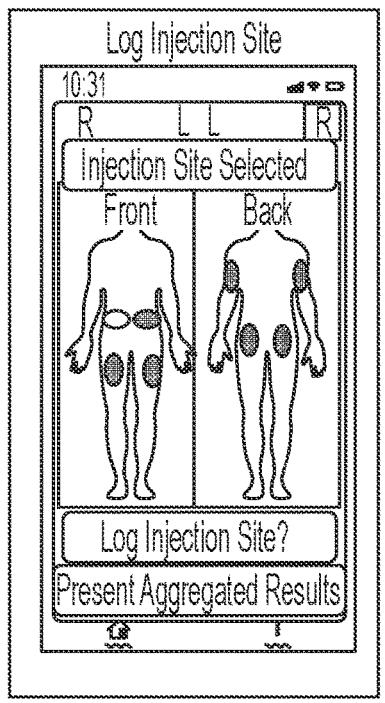

If user presses the button labeled "Proceed to Injection?", logic 900 advances to step 902, where external device 450 receives user input indicating a selected injection site. FIG. 10H provides an exemplary screenshot showing how external device 450 may receive this input. Here, the user is instructed to press one of the displayed injection sites on the front/back human body diagrams. In this example, the user has touched the right abdomen injection site. The external device 450 may provide feedback confirming the user's selected site, e.g., by adding a symbol to the selected site (a plus symbol, as shown in FIG. 10H), changing the color, size, weight, outlining, or other visual aspect of the selected site, and/or by providing a textual or audible confirmation. In some embodiments, the external device 450 may also confirm the user's selected site not by altering the appearance of the selected site, but by altering the appearance of all non-selected sites. One example of this embodiment is shown in FIG. 10I, in which the selected site (right abdomen) remains unchanged, but all non-selected sites are grayed out. FIG. 10I also includes a banner or notice at the top of the screen confirming to the user that the injection site has been selected.

At step 904, external device 450 receives injection event data indicating that an injection or dispensing event has occurred. As described herein, this injection event data may be conveyed from medication delivery device 20 to external device 450 via wireless BLE communication link 440. As previously described, this data may include information about the time of an injection event, the time that has elapsed since an injection event, the date of injection event, the temperature of a medication stored in the medication delivery device, the state of the skin contact sensors, or any other suitable data, as aspects of the techniques described herein are not limited in this respect. External device 450 assumes the injection event data received at step 904 pertains to an injection that was delivered to the injection site selected at step 902.

At step 906, external device 450 receives input indicating a level of injection pain actually experienced by the patient at the time of the injection. Device 450 may solicit this input from the user by prompting the user with a question, or series of questions. Alternatively, the user may provide such input without any affirmative prompting from device 450. The input received by device 450 may comprise a numerical score, manipulation of a slider or knob, or selection of one of a plurality of buttons or options indicative of the level of pain actually experienced by the patient.

Figure 10J:
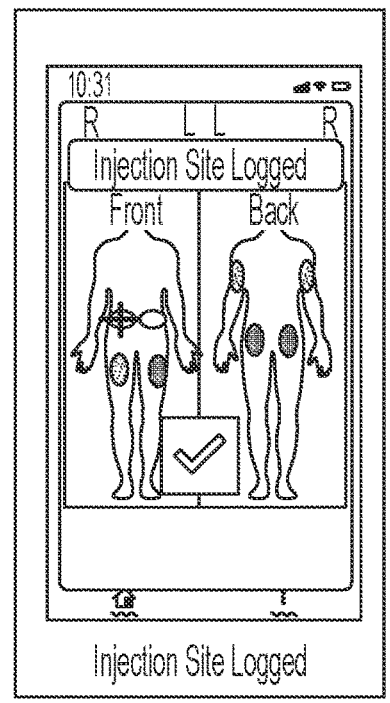

At step 908, external device 450 logs the injection event data received at step 904 in memory. The log may also include supplemental data that was computed by external device 450 based on the injection event data received at step 904, but which was not included in the injection event data. For instance, the injection event data may comprise data indicating that an amount of time that has elapsed since the injection event, e.g., in minutes or seconds. The external device 450 may consult a digital clock onboard the external device, determine based on the injection event data that an injection occurred at a specific time and/or date (e.g., 11:01 am Eastern Standard Time on Jun. 15, 2021), and include that determined time in the log entry. The log entry may also indicate that the injection event described by the injection event data was injected into the injection site selected at step 902. Additionally, or alternatively, the log entry may also indicate the level of injection pain actually experienced by the patient at the time of the injection, as received at step 906. In general, at this step, device 450 associates the injection event data received at step 904 with the injection site selected at step 902 and/or the injection site pain data received at step 906. This association may take the form of a volatile or non-volatile record stored in the memory of device 450. In some embodiments, external device 450 may display a confirmation screen (e.g., as shown in FIG. 10J) informing the user that the injection event, selected injection site, and/or indicated level of injection site pain has been successfully logged.

At step 910, external device 450 waits for a pre-programmed time period, such as 1-3 hours. As used herein, "pre-programmed" does not mean a value may not be altered after initial programming. For example, in some embodiments, the pre-programmed time period may be modified by a user, such as a caregiver or a patient. Also, in some embodiments, external device 450 may automatically apply different pre-programmed time periods depending on different factors, such as the type of injection device, medication being injected, injection site selected, time of day, patient data (e.g., patient medical or biographical data), patient preferences, and the like. At step 912, external device 450 receives additional input indicating a level of injection pain experienced by the patient at the injection site that received the injection event. As before, device 450 may solicit this input from the user by prompting the user with a question, or series of questions. The input received by device 450 may comprise a numerical score, manipulation of a slider or knob, or selection of one of a plurality of buttons or options indicative of the level of pain actually experienced by the patient. This delayed user input may be indicative of a level of pain caused by any post-injection reaction of the patient's tissue at the injection site.

At step 914, external device updates the injection event log entry saved at step 908 with the additional user input provided at step 912. Logic 900 ends after step 914.

Upon the conclusion of logic 900, external device 450 may retain a log of the time/date of the completed injection event, the injection site that received the injection event, the level of pain reported by the patient at the time of the injection, and/or the level of pain reported by the patient 1-3 hours after the end of the injection, as previously described. The next time the patient launches logic 900 (e.g., by launching a mobile application, or by initiating a feature in such mobile application), this data may be used to update or supplement the initial guidance previously described in relation to step 904. As the patient continues to perform and log injections using logic 800 and 900, the data in the aforementioned log provides increasingly detailed and specific data regarding injection site pain experienced by the patient which may be used to generate this initial guidance. In this way, while external device 450's initial guidance may be based on population-level averages (or device 450 may default to providing no guidance at all), as the patient continues to use logic 800 and 900 to perform injections, device 450 "learns" from the user's past experiences with injections to provide increasingly tailored guidance regarding expected injection pain that is specific to the patient.

For instance, the initial guidance provided at step 804 may be similar to the guidance provided to the user at step 901, after capacitance data has been collected during implementation of logic 700 and 900. In some embodiments, the guidance provided at step 901 may be further modified and/or augmented by the level of pain previously reported by the patient at steps 906 and 914. If the external device 450 had predicted a first level of pain based on capacitance data for the right abdomen injection site, for example, but if the patient reported actually experiencing a different level of pain at the time of the injection (or 1-3 hours after the injection), the expected level of pain for the right abdomen may be changed to reflect the patient's actually experienced pain.

The data captured by the log of patient-reported injection site pain, either at the time of injection and/or 1-3 hours after the injection, may also be used in other ways. For example, the patient-reported injection site pain may be used to characterize the patient's pain tolerance. If the patient reports relatively low injection site pain (either at the time of injection or some time after the injection, and potentially across multiple injections), the patient may be classified as having relatively high pain tolerance. Conversely, if the patient reports relatively high injection site pain (either at the time of injection or some time after the injection, and potentially across multiple injections), the patient may be classified as having relatively low pain tolerance. This may be an important insight for a healthcare provider advising or providing care to the patient. In some cases, to better control for variations in how different patients report their injection site pain, the variations in pain scores reported by patients may be compared with variations in measured capacitance at different injection sites to classify patients as having relatively high or relatively low pain tolerance. In this embodiment, a patient having high pain tolerance may be expected to report pain scores that do not vary very much from each other (e.g., are uniformly low), even though different injection sites on the patient's body exhibit large measured capacitance differences. Conversely, a patient having low pain tolerance may be expected to report pain scores having significantly higher variance (e.g., range from low to high), especially if different injection sites on the patient's body exhibit large measured capacitance differences. In yet other cases, a patient having very low pain tolerance may be expected to report pain scores having low variance, but which are uniformly high. As such, variations in pain scores reported by a patient may also be used, either alone or in combination with the absolute score values, to classify patients as having relatively high or relatively low pain tolerance.

Alternatively, or in addition, the data captured by the log of the patient-reported injection site pain, either at the time of injection and/or 1-3 hours after the injection, may be used to compare pain caused by different drug products, by different formulations of a drug product, or even by different batches of the same drug product. For example, a first set of subjectively experienced and self-reported pain scores may be collected from a population of patients that self-administered a first drug type (or first drug formulation, or a first batch of drug), and a second set of pain scores may be collected from a similar (or same) population of patients that self-administered a second drug (or second drug formulation, or a second batch of drug). The first and the second set of subjectively experienced and self-reported pain scores may be compared to derive insights regarding which drug (or drug formulation, or batch of drug) led to greater or less injection site pain. In cases where a different batches of drugs are compared against each other, batches may differ from each other in any of a plurality of ways. For example, the batches may be manufactured in different ways, or stored, manufactured, or handled in different ways, exposed to different conditions (e.g., temperature changes), and other differences. The method presented in FIG. 9 for collecting subjectively experienced and reported pain scores from injection site pain may be used to derive insights regarding how injection site pain differs across any of the aforementioned dimensions.

In some embodiments, in addition to or as an alternative to providing guidance about expected injection site pain, external device 450 may provide guidance regarding an expected level of pharmaceutical effectiveness of medication injected into different injection sites. The inventors have appreciated that the same type and amount of injected medication may result in different levels of pharmacokinetic/pharmacodynamic (PK/PD) effectiveness (also referred to herein as pharmaceutical effectiveness) based on the injection site. For instance, injecting medication into the abdomen may result in greater or lesser PK/PD effectiveness compared to injecting the same medication into the thigh or the upper arm. The way in which PK/PD effectiveness differs by injection site may also change depending on the type of drug being injected. For example, while one type of drug may exhibit greater PK/PD effectiveness when injected into the abdomen, another type of drug may exhibit greater PK/PD effectiveness when injected into the thigh. The way that PK/PD effectiveness differs by injection site for a specific type of drug may be experimentally observed in clinical trials. It would therefore also be desirable for external device 450 to provide and/or integrate guidance regarding which injection sites may provide greater PK/PD effectiveness.

Figure 10K:
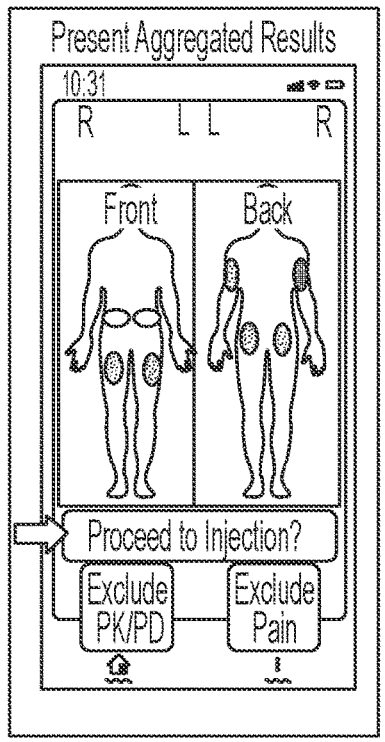

FIG. 10K presents an exemplary screenshot that presents the overall suitability of different injection sites based on both (i) an expected level of PK/PD effectiveness of medication injected into each site and (ii) an expected level of injection pain associated with each site. Lighter colored sites indicate more suitable injection sites, while darker colored sites indicate less suitable injection sites. In this embodiment, the PK/PD effectiveness of each site may be based on experimental data for a particular type of drug gathered in clinical trials and pre-programmed into external device 450. For example, if clinical trails establish that, for a particular type of medication, medication injected into the abdomen exhibit high PK/PD effectiveness, medication injected into the upper arm or buttock exhibit medium PK/PD effectiveness, and medication injected into the thigh exhibit low PK/PD effectiveness, this data may be pre-programmed into external device 450. The shadings of different injection sites on FIG. 10K may be based on a weighted combination of PK/PD effectiveness and expected injection site pain. The weighting between PK/PD effectiveness and expected injection site pain may be a pre-programmed and/or configurable parameter.

In this embodiment, if the user presses the button "Exclude PK/PD" at the bottom of FIG. 10K, the shadings in FIG. 10K may change by excluding PK/PD effectiveness data and may instead present expected injection pain data only. If the user presses the button "Exclude pain", the shadings in FIG. 10K may change by excluding injection pain data and may instead present PK/PD effectiveness data only. In yet other embodiments, the screenshot in FIG. 10K may be further modified to provide the user an option to adjust the weighting used to combine PK/PD effectiveness and expected injection site pain.

Although logic 700, 800, and 900 have been described above with respect to embodiments where a drug-delivery device 20 is in wireless communication with an external device 450, the above-described logic may be modified to be implemented on drug-delivery device 20 alone. As previously described, drug-delivery device 20 may be equipped with devices 432 for providing user feedback, such as one or more indicator lights, a display, a haptic indicator, and/or a speaker for providing auditory feedback. In some alternative embodiments, the drug-delivery device 20 may be incorporate a display screen that displays screenshots similar to those discussed previously in relation to FIGS. 10A-K. In other embodiments, the aforementioned pain and/or suitability/desirability indications may be delivered using one or more light emitting diodes (LEDs). For example, device 20 may be provided with a plurality of LEDs, wherein each LED corresponds to a different injection site on the user's body. As capacitance data for each injection site is gathered, and/or as patient reported experiences associated with each injection site is gathered, the LEDs corresponding to each injection site on device 20 may change color to indicate a level of expected pain level, and/or a level of suitability/desirability for each injection site based on expected PK/PD effectiveness and/or pain, as described herein. In other embodiments, device 20 may be provided with a single LED that changes color depending on capacitance data gathered by the capacitance sensors—in such embodiments, device 20 may only provide an expected pain level only one injection site at a time. In yet other embodiments, device 20 may be provided with a small speaker for providing audible messages to a user, providing the aforementioned pain and/or suitability/desirability indications. All of the embodiments described herein for providing the aforementioned indications are not exclusive and any or all of these embodiments may be employed together; for instance, a device 20 may be configured to both communicate with an external device 450 as well as provide indications via one or more LEDs.

The terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

Various aspects are described in this disclosure, which include, but are not limited to, the following aspects:

1. A method for evaluating injection sites on a body of a patient, the method comprising: receiving, at a processing circuit in communication with one or more capacitance sensors positioned at a potential injection site on the body of the patient, a signal indicative of a capacitance of body tissue at the potential injection site measured by the one or more capacitance sensors; and determining, by the processing circuit based on the received signal, a level of expected pain that would be experienced by the patient from a prospective injection at the potential injection site.

2. The method of aspect 1, wherein the one or more capacitance sensors are disposed on a drug-delivery device comprising a drug, and the processing circuit is disposed at a mobile device in wireless communication with the drug-delivery device.

3. The method of any one of aspects 1-2, further comprising presenting, by the processing circuit, an indication to a user of the determined level of expected pain via at least one of a visual indication from a light emitting diode (LED), a visual indication on a display screen, an audible indication, and a haptic indication.

4. The method of aspect 3, wherein the indication comprises a color-coded diagram of at least a portion of a human body on the display screen.

5. The method of any one of aspects 1-4, further comprising generating, by the processing circuit, an indication of overall suitability of the potential injection site based on both (i) the determined level of expected pain and (ii) a pre-programmed level of expected pharmaceutical effect that would be experienced by the patient from the prospective injection at the potential injection site.

6. The method of any one of aspects 1-5, further comprising receiving, at the processing circuit, user input from the patient indicative of at least one of a level of pain actually experienced by the patient at a time of an actual injection at the potential injection site and a level of pain actually experienced by the patient at a pre-programmed time after the time of the actual injection.

7. The method of aspect 6, wherein the pre-programmed time is greater than or equal to 1 hour after the actual injection, and less than or equal to 3 hours after the actual injection.

8. The method of any one of aspects 6-7, further comprising modifying the determined level of expected pain based on previously-received user input.

9. The method of aspect 3, wherein the potential injection site is a first potential injection site, the method further comprising: receiving, at the processing circuit, a signal indicative of a capacitance of body tissue at a second potential injection site on the body of the patient measured by the one or more capacitance sensors; wherein the presented indication comprises an indication whether the level of expected pain that would be experienced by the patient from the prospective injection at the first potential injection site is expected to be greater or less than a level of expected pain that would be experienced by the patient from a prospective injection at the second potential injection site.

10. The method of aspect 9, further comprising injecting a medication at one of the first and second potential injection sites based on the generated indication.

11. A processing device for evaluating injection sites on a body of a patient, the device comprising: a memory storing instructions; a communication interface configured to receive data from one or more capacitance sensors; a processing circuit configured to execute the instructions to: receive, from the one or more capacitance sensors via the communication interface, data indicative of a capacitance of body tissue at a potential injection site on the body of the patient measured by the one or more capacitance sensors, store the received data indicative of the capacitance in the memory, and determine, based on the received data indicative of the capacitance, a level of expected pain that would be experienced by the patient from a prospective injection at the potential injection site.

12. The processing device of aspect 11, wherein the measurement device is a drug-delivery device comprising a drug.

13. The processing device of any of aspects 11-12, further comprising a display screen, wherein the processing circuit is further configured to present an indication to a user of the determined level of expected pain via the display screen.

14. The processing device of aspect 13, wherein the indication comprises a color-coded diagram of at least a portion of a human body.

15. The processing device of any one of aspects 11-14, wherein the processing circuit is further configured to generate an indication of overall suitability of the potential injection site based on both (i) the determined level of expected pain and (ii) a pre-programmed level of expected pharmaceutical effect that would be experienced by the patient from the prospective injection at the potential injection site.

16. The processing device of any one of aspects 11-15, wherein the processing circuit is further configured to solicit and receive user input from the patient indicative of at least one of a level of pain actually experienced by the patient at a time of an actual injection at the potential injection site and a level of pain actually experienced by the patient at a pre-programmed time after the time of the actual injection.

17. The processing device of aspect 16, wherein the pre-programmed time is greater than or equal to 1 hour after the actual injection, and less than or equal to 3 hours after the actual injection.

18. The processing device of any of aspects 16-17, wherein the processing circuit is further configured to modify the determined level of expected pain based on previously-received user input.

19. The processing device of aspect 13, wherein: the potential injection site is a first potential injection site; the processing circuit is further configured to receive data indicative of a capacitance of body tissue at a second potential injection site measured by the one or more capacitance sensors; and the presented indication comprises an indication whether the level of expected pain that would be experienced by the patient from the prospective injection at the first potential injection site is expected to be greater or less than a level of expected pain that would be experienced by the patient from a prospective injection at the second potential injection site.

20. A system for evaluating injection sites on a body of a patient, the system comprising: an injection device comprising: a needle for delivering a medication to the patient via an injection, one or more capacitance sensors, and a wireless transmitter; and an external device comprising: a memory storing instructions; a communication interface configured to receive data from the wireless transmitter of the injection device; and a processing circuit configured to execute the instructions to: receive, via the communication interface, data from the injection device indicative of a capacitance of body tissue at a potential injection site on the body of the patient measured by the one or more capacitance sensors, store the received data indicative of the capacitance in memory, and determine, based on the received data indicative of the capacitance, a level of expected pain that would be experienced by the patient from a prospective injection by the injection device at the potential injection site.

21. The system of aspect 20, wherein the external device further comprises a display screen, wherein the processing circuit is further configured to present an indication to a user of the determined level of expected pain via the display screen.

22. The system of any one of aspects 20-21, wherein the processing circuit is further configured to: receive, via the communication interface, data from the injection device indicative of an actually-delivered injection and an actual injection site associated with the actually-delivered injection; and associate the actual injection site with a log entry for the actually-delivered injection, the log entry comprising at least one of a time and date associated with the actually-delivered injection.

23. The system of aspect 22, wherein the processing circuit is further configured: to solicit and receive user input from the patient indicative of at least one of a level of pain actually experienced by the patient at a time of the actually-delivered injection at the actual injection site and a level of pain actually experienced by the patient at a pre-programmed time after the time of actual injection; and associate the received user input with the log entry for the actually-delivered injection.

24. The system of aspect 23, wherein the processing circuit is further configured to modify the determined level of expected pain based on previously-received user input.

25. The system of any one of aspects 20-24, wherein the injection device further comprises a reservoir holding the medication.

What is claimed is:

1. A method for evaluating injection sites on a body of a patient, the method comprising:
    positioning one or more capacitance sensors at a potential injection site on the body of the patient;
    sending, to a processing circuit, a signal indicative of a capacitance of body tissue at the potential injection site measured by the one or more capacitance sensors;
    determining, by the processing circuit based on the received signal, a level of expected pain that would be experienced by the patient from a prospective injection at the potential injection site; and
    injecting a medication at the potential injection site based on the determination by the processing circuit.

2. The method of claim 1, further comprising outputting, by the processing circuit, a signal that presents an indication to a user of the determined level of expected pain via at least one of a visual indication from a light emitting diode (LED), a visual indication on a display screen, an audible indication, and a haptic indication.

3. The method of claim 2, wherein the indication comprises a color-coded diagram of at least a portion of a human body on the display screen.

4. The method of claim 1, further comprising generating, by the processing circuit, an indication of overall suitability of the potential injection site based on both (i) the determined level of expected pain and (ii) a pre-programmed level of expected pharmaceutical effect that would be experienced by the patient from the prospective injection at the potential injection site.

5. The method of claim 1, further comprising receiving, at the processing circuit, user input from the patient indicative of at least one of a level of pain actually experienced by the patient at a time of an actual injection at the potential injection site and a level of pain actually experienced by the patient at a pre-programmed time after the time of the actual injection.

6. The method of claim 5, wherein the pre-programmed time is greater than or equal to 1 hour after the actual injection, and less than or equal to 3 hours after the actual injection.

7. The method of claim 5, further comprising modifying the determined level of expected pain based on previously-received user input.

8. The method of claim 2, wherein the potential injection site is a first potential injection site, the method further comprising:
    sending, to the processing circuit, a signal indicative of a capacitance of body tissue at a second potential injection site on the body of the patient measured by the one or more capacitance sensors;
    wherein the presented indication comprises an indication whether the level of expected pain that would be experienced by the patient from the prospective injection at the first potential injection site is expected to be greater or less than a level of expected pain that would be experienced by the patient from a prospective injection at the second potential injection site.

9. A method for evaluating injection sites on a body of a patient, the method comprising:
    positioning one or more capacitance sensors at a first potential injection site on the body of the patient;
    sending, to a processing circuit, a first signal indicative of a capacitance of body tissue at the first potential injection site measured by the one or more capacitance sensors;
    positioning the one or more capacitance sensors at a second potential injection site on the body of the patient;
    sending, to the processing circuit, a second signal indicative of a capacitance of body tissue at the second potential injection site measured by the one or more capacitance sensors;
    determining, by the processing circuit, based on the first signal and the second signal, whether a level of expected pain that would be experienced by the patient from a prospective injection at the first potential injection site is expected to be greater or less than a level of expected pain that would be experienced by the patient from a prospective injection at the second potential injection site; and
    injecting a medication at one of the first and second potential injection sites based on the determination by the processing circuit.

* * * * *